(12) United States Patent
Wu

(10) Patent No.: US 6,969,532 B2
(45) Date of Patent: Nov. 29, 2005

(54) COMPOUNDS INHIBITING COX-2 AND INOS PROMOTER ACTIVITIES

(75) Inventor: Kenneth K. Wu, 2007 Swift Blvd., Houston, TX (US) 77030

(73) Assignees: Kenneth K. Wu, Houston, TX (US); W. Wayne Liauh, Honolulu, HI (US)

( * ) Notice: Subject to any disclaimer, the term of this patent is extended or adjusted under 35 U.S.C. 154(b) by 0 days.

(21) Appl. No.: 09/920,121

(22) Filed: Jul. 31, 2001

(65) Prior Publication Data

US 2002/0015739 A1 Feb. 7, 2002

Related U.S. Application Data

(60) Provisional application No. 60/225,671, filed on Aug. 1, 2000.

(51) Int. Cl.[7] .................................................. C12N 5/00
(52) U.S. Cl. ........................ 424/572; 424/520; 435/325; 435/366; 435/190; 514/1
(58) Field of Search ................................ 424/572, 520; 435/325, 366, 190; 514/1

(56) References Cited

U.S. PATENT DOCUMENTS 5,776,967 A * 7/1998 Kreft et al.
5,869,524 A * 2/1999 Failli
6,140,515 A * 10/2000 Chen et al.

* cited by examiner

*Primary Examiner*—Leon B. Lankford, Jr.
(74) *Attorney, Agent, or Firm*—M. Wayne Liauh

(57) ABSTRACT

A new chemical compound for treating human inflammatory diseases, tissue damage, stroke, septic shock and cancer. This chemical compound is produced from a process including the following steps: (a) washing human foreskin fibroblasts with a fresh DMEM medium then incubated in a fresh medium containing 2.5%–10% fetal bovine serum for at least 8 hours to form a proliferating phase medium (PPM); (b) subjecting the proliferating phase medium to a 10-kDa ultrafiltration membrane to separate the proliferating phase medium into a <10 kDa fraction, which passes through the 10-kDa ultrafiltration membrane, and a >10 kDa fraction, which is retained by the 10-kDa ultrafiltration membrane; (c) Chromatographing the <10 kDa fraction on a Superdex 30 column by FPLC to separate the <10 kDa fraction into five post-FPLC fractions; (d) Injecting the second post-FPLC fraction into a $C_{18}$ column in a HPLC system with a gradient elute from 10% to 50% acetonitrile and water containing 0.1% trifluoroacetic acid, to separate the second post-FPLC fraction into five post-HPLC fractions; and (e) collecting the fourth post-FPLC fraction for further purification. Fluorescence spectroscopy shows that this product is a derivative of trypophan or trypophan-like, and mass spectrometry indicates that it has a molecular weight of about 604 daltons with a minor peak having a molecular weight of about 779 daltons.

4 Claims, 8 Drawing Sheets

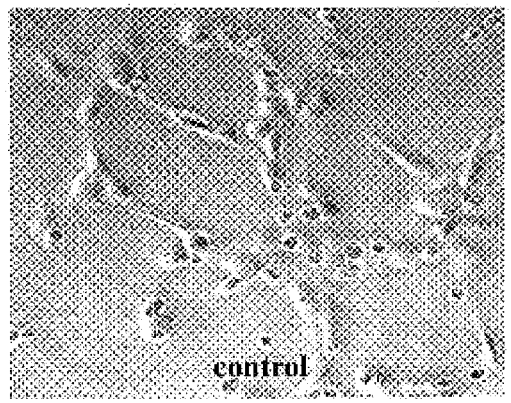
Fig. 10A
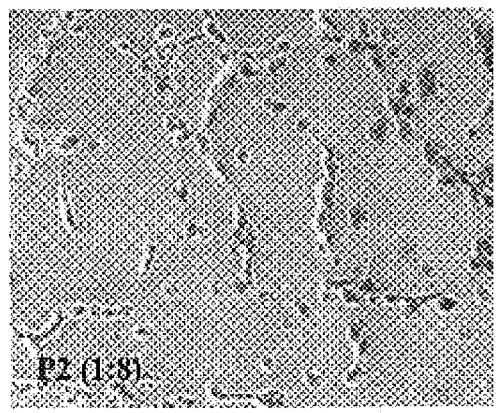
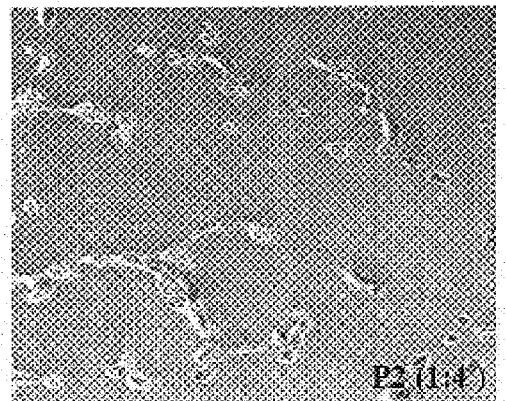
Fig. 10B　　　　Fig. 10C
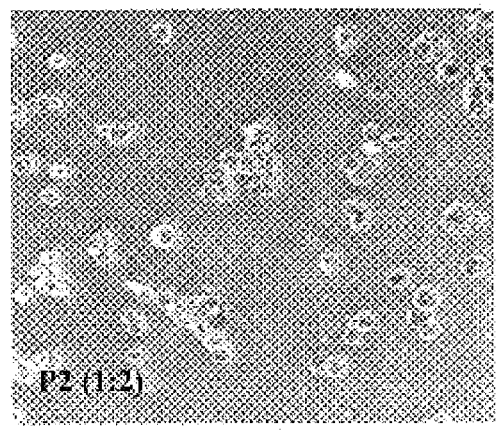
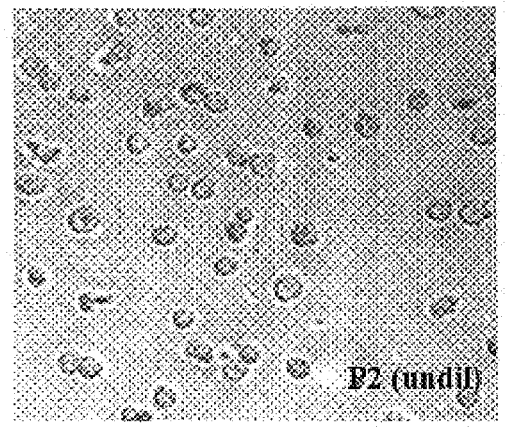
Fig. 10D　　　　Fig. 10D

COMPOUNDS INHIBITING COX-2 AND iNOS PROMOTER ACTIVITIES

This application claim benefit to provisional application No. 60/225,671 Aug. 1, 2000.

FIELD OF THE INVENTION

The present invention relates to compounds which exhibit concurrent COX-2 and iNOS suppressing activities. More specifically, the present invention relates to compounds that block the expressions of both COX-2 and iNOS so as thereby to effectively treat the consequent diseases including inflammation, tissue injury, septic shock and cancer growth. Because of the complexity of their molecular structure, the present invention utilizes a finger-printing procedure to describe these compounds, i.e., by describing in detail the process steps these compounds can be reproducibly produced.

BACKGROUND OF THE INVENTION

COX-2 is an inducible enzyme expressed in inflammatory neoplastic and neuronal cells. It occupies a central position in synthesizing prostaglandins and thromboxane $A_2$. Several prostaglandins such as prostaglandin $E_2$ and $E_2$ mediate inflammation. Selective inhibition of COX-2 suppresses inflammatory reactions and pain. Selective COX-2 inhibitors such as Celebrex® and Vioxx® prove to be efficacious anti-inflammatory drugs with less adverse effects than other nonsteroidal anti-inflammatory drugs. COX-2 has recently been shown to be causally associated with adenomatous polyposis, a precancerous hereditary disorder and colon cancer. Selective COX-2 inhibitors not only suppress experimental adenomatous polyposis and colon cancer in mice and rats but also reduce human adenomatous polyposis in a randomized clinical trial. However, the extent of polyp reduction by Celebrex® from this clinical trial was small, about 30%, suggesting the involvement of other factors. COX-2 causes cancer growth by several possible mechanisms. COX-2 overexpression in the stromal cells within a cancer mass induces new blood vessel formation (angiogenesis) which provides nutrition for tumor cell growth. COX-2 overexpression increases synthesis of metalloproteinase inhibitors which promotes cancer cell metastasis. It has also been reported that COX-2 stimulates cell proliferation. In summary, COX-2 plays a key role in inflammation, tissue injury and cancer growth.

iNOS (also known as NOS 2) is also an inducible enzyme expressed in macrophages, smooth muscle cells and liver cells. It catalyzes the synthesis of a large quantity of nitric oxide (NO) which forms peroxynitrite with superoxide. Peroxynitrite causes tissue injury and apoptosis. Reactive nitrogen species are also formed from NO, which also causes tissue damage. Proteins and DNA can be nitrosylated by NO. iNOS has been shown to play a key role in the pathogenesis of septic stroke, stroke, myocardial infarction, inflammation. NO can also induce angiogenesis thereby increasing tumor cell growth. Several classes of inhibitors of nitric oxide synthase are available but they are not isoform specific. There is an active research effort to develop iNOS-specific inhibitors.

COX-2 and iNOS are induced concurrently when cells and tissues are stimulated with certain environmental insults. They can be expressed in the same cells or in different cells located within the same affected tissues. Their products act in a concerted manner to promote inflammation, tissue injury, septic shock and tumorigenesis. Treatment for these important human diseases relies on drugs that inhibit a single mediator of the complex pathophysiological processes, and so far has had only limited successes.

SUMMARY OF THE INVENTION

The primary object of the present invention is to develop new compounds for treating inflammatory disorders, septic shock, tumor growth and tissue injuries. More specifically, the primary object of the present invention is to overcome the drawbacks in the currently available treatment of inflammatory disorders, septic shock, tumor and tissue injuries by providing new compounds that have a more fundamental basis for controlling these pathophysiological processes and therefore will be more efficacious in treating inflammation, septic shock, tissue injury, and malignant diseases such as colon cancer. The novel compounds disclosed in the present invention can effectively block the expressions of both COX-2 and iNOS. Because of the complexity of their molecular structure, the present invention utilizes a finger-printing procedure to describe these compounds, by describing in detail the process steps for producing those compounds which exhibit the concurrent COX-2 and iNOS suppressing activities.

In summary, the inventor of the present invention has discovered a new product which exhibits concurrent COX-2 and iNOS suppressing activities and which is purified from a cultured medium produced from a process that comprises the following steps:

(1) washing human foreskin fibroblasts with a fresh DMEM medium then incubated in a fresh medium containing 2.5%–10% fetal bovine serum for at least 8 hours to form a proliferating phase medium (PPM);

(2) subjecting the proliferating phase medium to a 10-kDa ultrafiltration membrane to separate the proliferating phase medium into a <10 kDa fraction, which passes through the 10-kDa ultrafiltration membrane, and a >10 kDa fraction, which is retained by the 10-kDa ultrafiltration membrane;

(3) Chromatographing the <10 kDa fraction on a Superdex 30 column by FPLC to separate the <10 kDa fraction into first, second, third, fourth, and fifth post-FPLC fractions, which are observed as five peaks at a spectra absorbance at 220 nm and numbered based on their elusion times from the Superdex 30 column;

(4) Injecting the second post-FPLC fraction into a $C_{18}$ column in a HPLC system with a gradient elute from 10% to 50% acetonitrile and water containing 0.1% trifluoroacetic acid, to separate the second post-FPLC fraction into first, second, third, fourth, and fifth post-HPLC fractions, which are observed as five peaks at a spectra absorbance at 220 nm and numbered based on their elusion times from the $C_{18}$ column; and (5) collecting said fourth post-HPLC fraction.

It was discovered by the inventor of the present invention that human foreskin fibroblasts at the proliferative phase produce substances that inhibit the COX-2 messenger RNA and protein levels induced byphorbol 12-myristate 13-acetate (PMA) or interleukin-1β (IL-1β). The experiments were done as follows. Human foreskin fibroblasts were cultured in media deprived of fetal bovine serum for 24 hours. A vast majority (>90%) of these cells were in the $G_0$ phase (quiescent cells) as determined by flow cytometry. The media were removed and replaced with fresh media containing 10% fetal bovine serum. These cells entered the S phase of cell cycle at 16 hour. The conditioned culture media were collected and their ability to inhibit COX-2 and iNOS protein expressions was tested in a fibroblast and macrophage assay systems, respectively. COX-2 proteins induced by PMA or IL-1β in quiescent fibroblasts were suppressed by the conditioned medium by 50%. iNOS proteins in macrophages were similarly inhibited by the conditioned media.

The inventor has performed five independent experiments and the results are reproducible. In contrast, media obtained from quiescent fibroblasts did not inhibit COX-2 or iNOS expression. These findings indicate that the conditioned media from S phase fibroblasts contain active substances that inhibit COX-2 protein and iNOS protein levels in cells. The inventor also next took steps to isolate the active compounds by membrane filtration, FPLC, and HPLC. Membrane filtration (using a membrane with a molecular weight cut-off of 10,000 dalton) showed that active compounds had molecular weight less than 10,000 daltons. The active compounds therefore comprise peptides or non-peptide small molecules.

Further separation by FPLC revealed 5 peaks detected at 200 nm (Example A1). Example A1 basically involves an FPLC elution profile of the active compounds from the membrane filtration. <10 K(i.e., less than 10,000 daltons) fraction of S phase fibroblast conditioned media was applied to FPLC and five fractions observed at an optical absorbance at 220 nm were detected. Fraction 2 has a molecular weight <4000 daltons. The molecular weight of fraction 5 is very small.

Example A2 tested the effect of FPLC fractions 1–5 on COX-2 protein expression induced by PMA (100 nM). Each fraction from FPLC was collected, concentrated and reconstituted with cultured media. 1 ml each of the reconstituted fractions was added to washed quiescent fibroblasts for 30 min. The cells were then stimulated with PMA for 4 h. Cells were lysed and identical quantities of cell lysates were loaded to an 8% polyacrylamide gel and proteins were separated by electrophoresis, transferred to a membrane and blotted with a specific COX-2 antibody. COX-2 protein bands were detected by a chemiluminescent system using a secondary antibody. Molecular markers were included to estimate the molecular weight of the resolved bands. The COX-2 bands were stripped and reblotted with an antibody to β-actin. Lane 1 is from fibroblasts without stimulation. Lane 2 is from cells pretreated with <10 K fraction of S phase conditioned media followed by PMA (100 nM). Lane 3 is from cells treated with PMA for 4 h. Lanes 4–8 are from cells pretreated with fractions 1–5 collected from FPLC (Example A1).

Fractions 1–5 representing the 5 peaks were collected and their activity on COX-2 protein expression induced by PMA (100 nM) was tested. Quiescent fibroblasts were pretreated with reconstituted fractions 1–5 followed by treatment with PMA for 4 h. COX-2 protein levels were determined by Western blot analysis. A Western blot representative of three separate experiments is shown in Example A2.

Lane 1 in Example A2 is the basal COX-2 protein level in unstimulated cells. Only a very trace amount of the COX-2 band was detected. Lane 2 is a positive control using the <10,000 dalton fraction. Quiescent fibroblasts were pretreated with this <10 K fraction for 30 min followed by PMA (100 nM) for 4 h. COX-2 proteins were reduced to the basal level. Lane 3 is quiescent fibroblasts treated with PMA for 4 h. A dense COX-2 band was detected. Lanes 4–8 represent the results of fractions 1–5 respectively. Pretreatment of fibroblasts with fraction 1 (lane 4), fraction 3 (lane 6) or fraction 4 (lane 7) did not reduce COX-2 protein levels. In contrast, COX-2 protein induced by PMA was reduced to baseline by fraction 2 (lane 5). COX-2 was only slightly reduced by fraction 5. Since fraction 5 (i.e., Example A1, peak 5) contained only small quantities of the original materials, compounds with high potency may be present. Reduction of COX-2 proteins by fraction 2 or 5 was not due to lading unequal quantities of fibroblast proteins since the β-actin proteins were equivalent (Example A2).

BRIEF DESCRIPTION OF THE DRAWING

The present invention will be described in detail with reference to the drawing showing the preferred embodiment of the present invention, wherein:

FIGS. 10A–E shows that the second fraction from the FPLC separation, P2, is effective in inhibiting tumor-induced angiogenesis.

DETAILED DESCRIPTION OF THE PREFERRED EMBODIMENT

Figure 1:
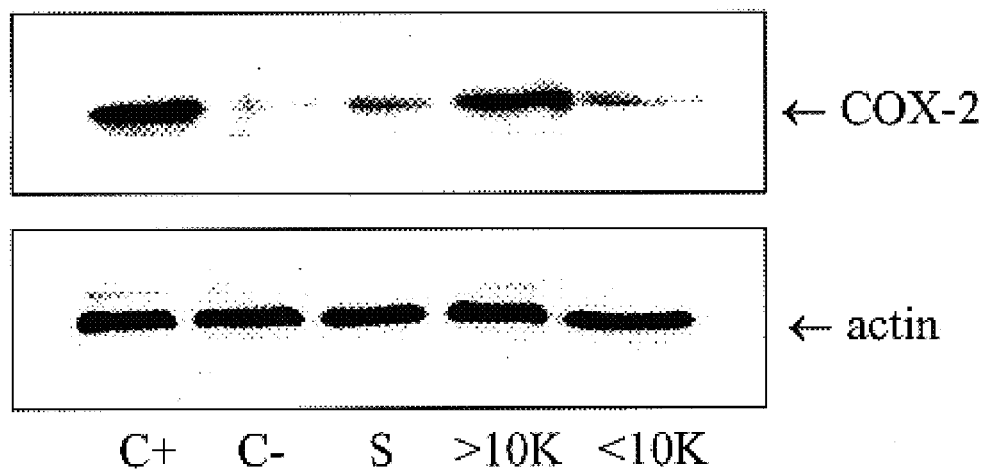
FIG. 1 shows the effects of filtration fractions from the S-phase medium on PMA-induced COX-2 expression in HFF.
Figure 3:
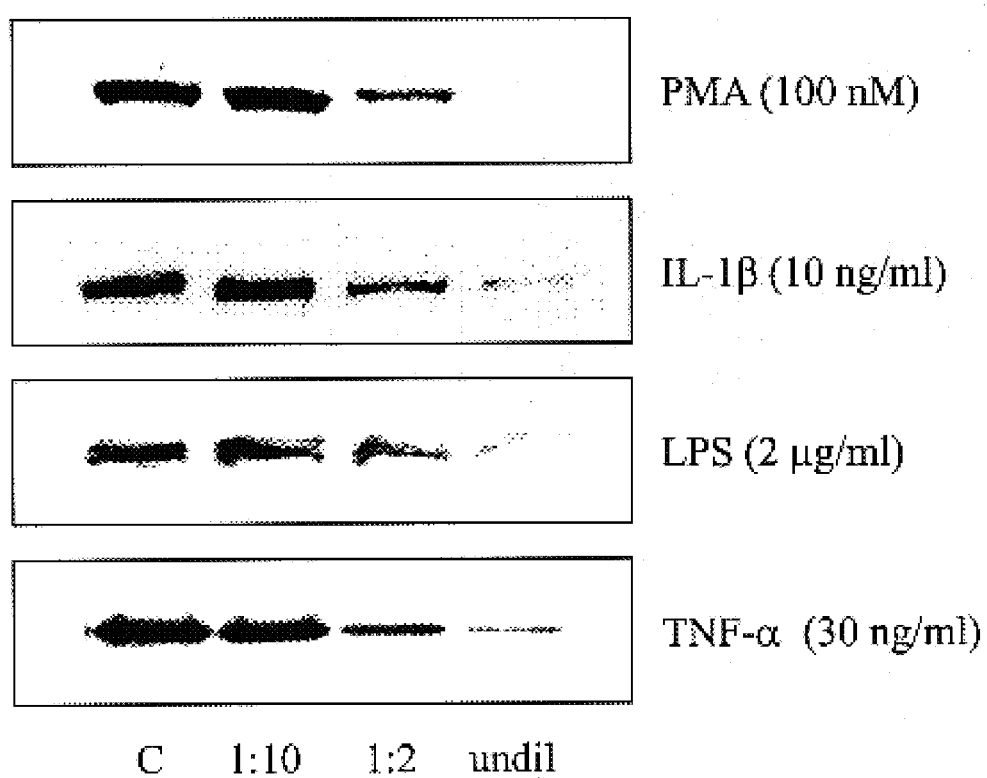
FIG. 3 shows the effects of the second fraction from the FPLC separation, P2, at various concentrations, on COX-2 levels induced by different regents in HFF.
Figure 2B:
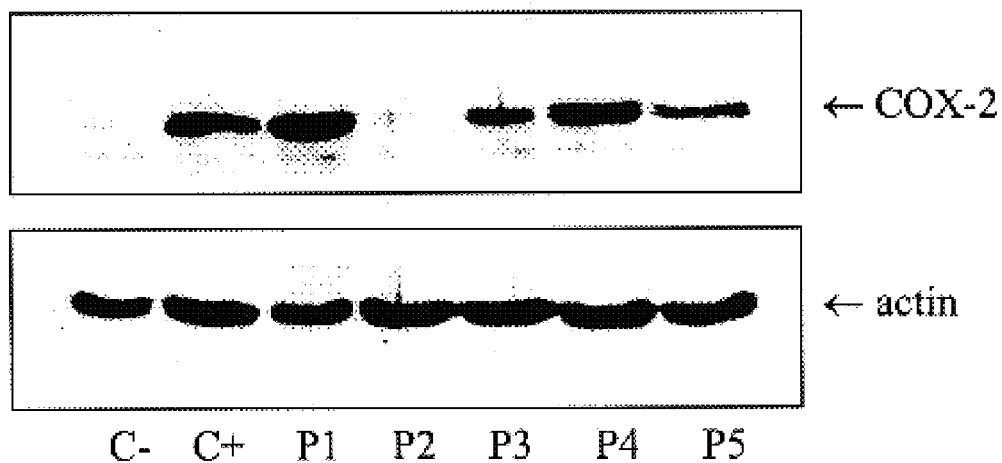
FIG. 2B shows the effects of the various post-FPLC fractions on PMA-induced COX-2 expression in HFF.
Figure 2A:
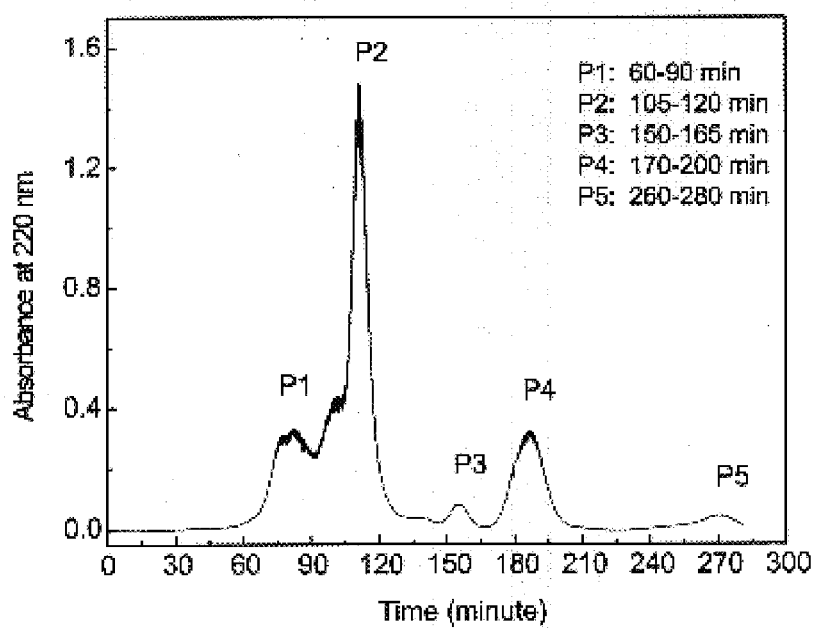
FIG. 2A shows fractions from the FPLC separation.
Figure 4:
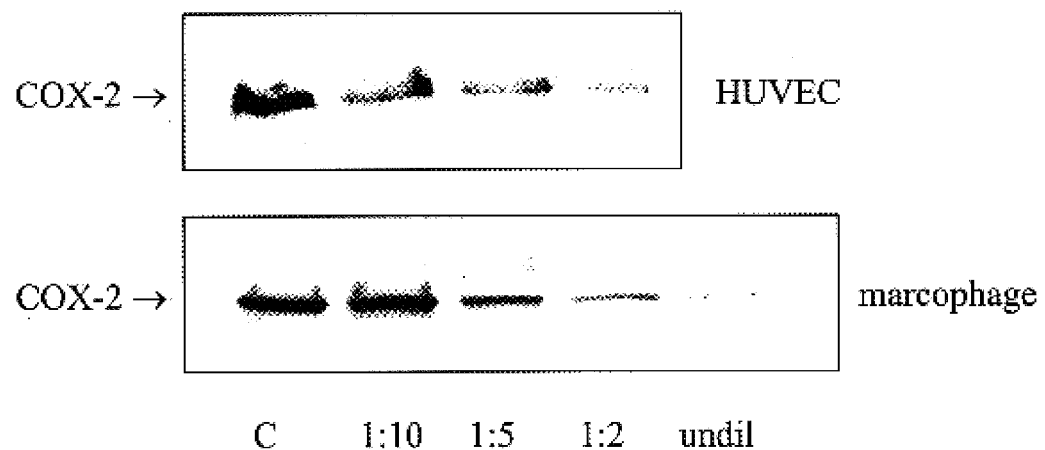
FIG. 4 shows the inhibition effect of the second fraction from the FPLC separation, P2, at various concentrations, on LPS-induced COX-2 levels in HUVEC and mouse marcophage.
Figure 5:
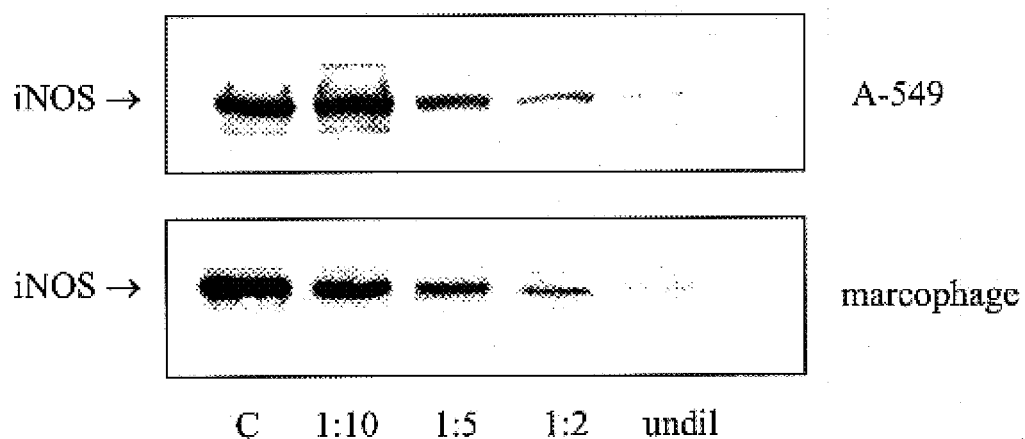
FIG. 5 shows the dose-dependent inhibition effect of the second fraction from the FPLC separation, P2, at various concentrations, on LPS-induced iNOS levels in mouse marcophage and human lung cancer A-549 cells.

The invention discloses a new compound for treating inflammatory disorders, septic shock, tumor growth and tissue injuries by currently inhibiting the expressions of both COX-2 and iNOS. Because of the complexity of their molecular structure, the present invention utilizes a fingerprinting procedure to describe these compounds, by describing in detail the process steps for producing those compounds which exhibit the concurrent COX-2 and iNOS suppressing activities.

As discussed above, the new treatment drug discovered in the present invention, which exhibits concurrent COX-2 and iNOS suppressing activities, is purified product from a cultured medium produced from a process that comprises the following steps:

(1) washing human foreskin fibroblasts with a fresh DMEM medium then incubated in a fresh medium containing 2.5%–10% fetal bovine serum for at least 8 hours to form a proliferating phase medium (PPM);

(2) subjecting the proliferating phase medium to a 10-kDa ultrafiltration membrane to separate the proliferating phase medium into a <10 kDa fraction, which passes through the 10-kDa ultrafiltration membrane, and a >10 kDa fraction, which is retained by the 10-kDa ultrafiltration membrane;

(3) Chromatographing the <10 kDa fraction on a Superdex 30 column by FPLC to separate the <10 kDa fraction into first, second, third, fourth, and fifth post-FPLC fractions, which are observed as five peaks at a spectra absorbance at 220 nm and numbered based on their elusion times from the Superdex 30 column;

(4) Injecting the second post-FPLC fraction into a $C_{18}$ column in a HPLC system with a gradient elute from 10% to 50% acetonitrile and water containing 0.1% trifluoroacetic acid, to separate the second post-FPLC fraction into first, second, third, fourth, and fifth post-HPLC fractions, which are observed as five peaks at a spectra absorbance at 220 nm and numbered based on their elusion times from the $C_{18}$ column; and (5) collecting the fourth post-HPLC fraction.

The present invention overcomes the drawbacks in the currently available treatment of inflammatory disorders, septic shock, tumor and tissue injuries by providing new compounds that have a more fundamental basis for controlling these pathophysiological processes and therefore will be more efficacious in treating inflammation, septic shock, tissue injury, and malignant diseases such as colon cancer.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1 AND COMPARATIVE EXAMPLE 1

Mammalian (including human) cells such as fibroblasts cultured in regular DMEM medium are washed 3 times with fresh medium without fetal bovine serum and incubated in serum-free medium for 24–48 hours. This procedure causes cells to exit the cell cycle and 90–95% cells are in $G_0$ (quiescent) phase of cell cycle. This is the control case and designated as Comparative Example 1.

In Example 1, cultured medium from quiescent cells is collected and stored. Cells are washed with fresh medium and incubated in fresh medium containing 2.5%–10% fetal bovine serum. After the cells have been incubated with serum-containing medium for 8 hours and longer, medium is removed and stored. The medium sample is designated proliferating phase medium (PPM) as contrasted with quiescent phase medium (QPM) collected above. PPM suppresses cyclooxygenase-2 (COX-2) protein and inducible nitric oxide synthase (iNOS) protein expressions whereas QPM does not. PPM contains a product released from proliferating cells that suppresses COX-2 and iNOS protein expression.

PP medium (typically 225 ml) is applied to a 10-kDa ultrafiltration membrane (Millipore). The fraction that filters through the membrane (molecular weight <10 kDa fraction) and the fraction that is retained above the filter (>10 kDa fraction) are collected. The lower molecular weight fraction (<10 kDa) suppresses COX-2 and iNOS protein expression whereas the higher molecular weight fraction has no such activity (FIG. 1). The <10 kDa fraction is next chromatographed on a Superdex 30 column by FPLC. To analyze peptide and small molecules in the chromatographed fractions, spectra at absorbance at 220 nm reveal 5 peaks and only peak 2 (P2) Figures COX-2 and iNOS suppressing activities (FIGS. 2–5).

Figure 6B:
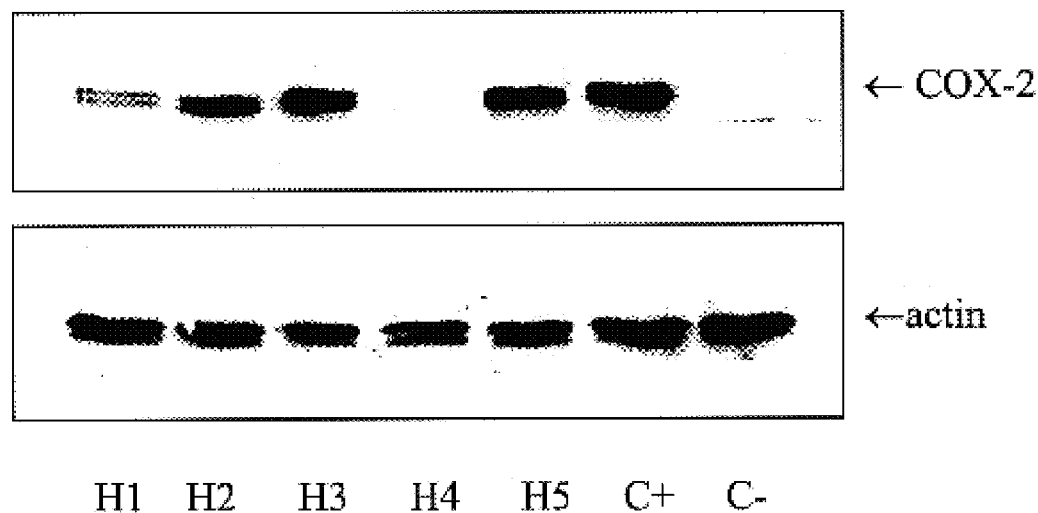
FIG. 6B shows the effects of the various post-HPLC fractions on PMA-induced COX-2 expression in HFF.
Figure 6A:
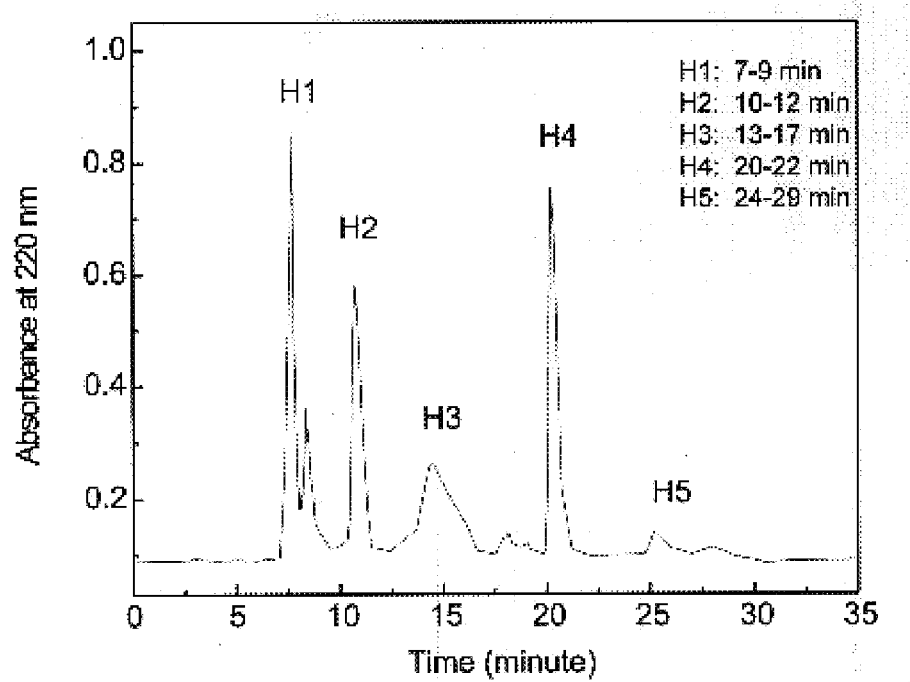
FIG. 6A shows fractions from the HPLC separation.

P2 fraction is injected into a $C_{18}$ column in a HPLC system with a gradient elute from 10% to 50% acetonitrile and water containing 0.1% trifluoroacetic acid. Five peaks with absorbance at 220 nm. The activity of each peak is tested and only peak 4 (H4) contains COX-2 and iNOS suppressing product (FIG. 6).

Figure 7A:
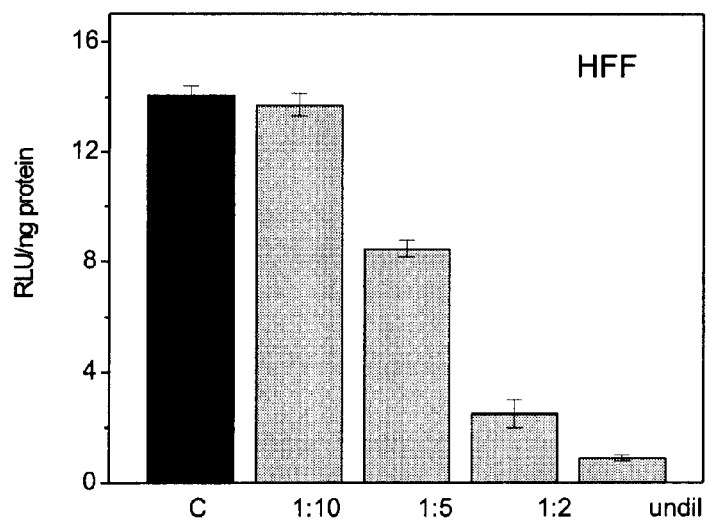
FIGS. 7A, 7B, 7C show the dose-dependent inhibition effect of the second fraction from the FPLC separation, P2, at various concentrations, on LPS-induced COX-2 promoter activity in HFF, HUVEC, and mouse marcophage, respectively.
Figure 7B:
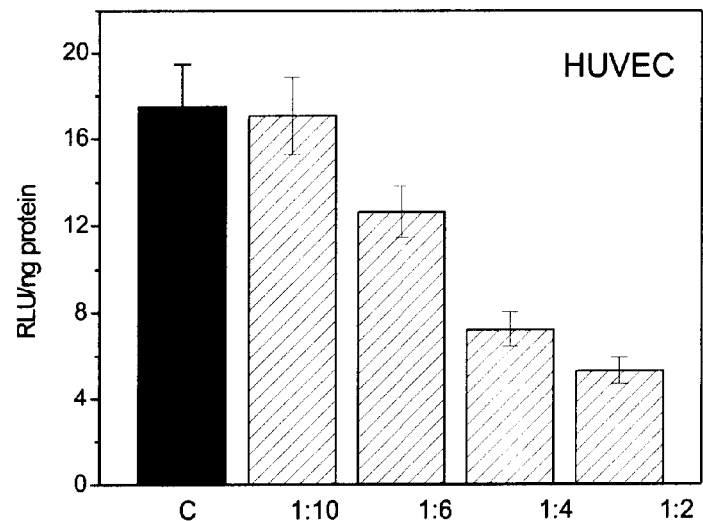
Figure 7C:
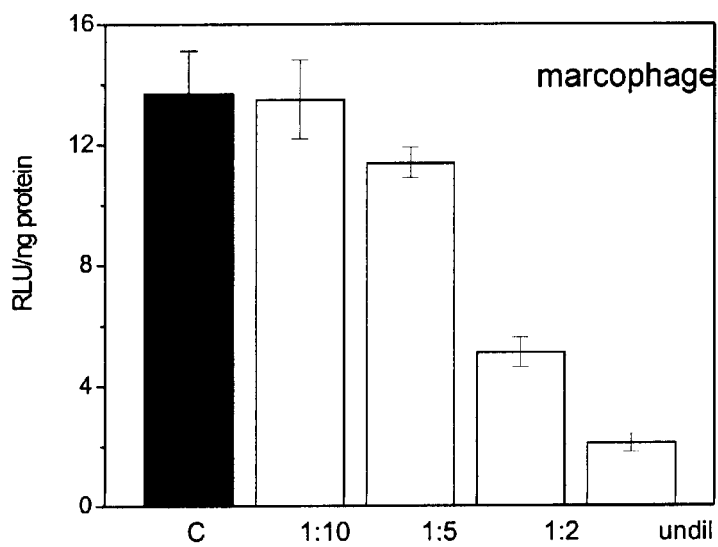
Figure 8A:
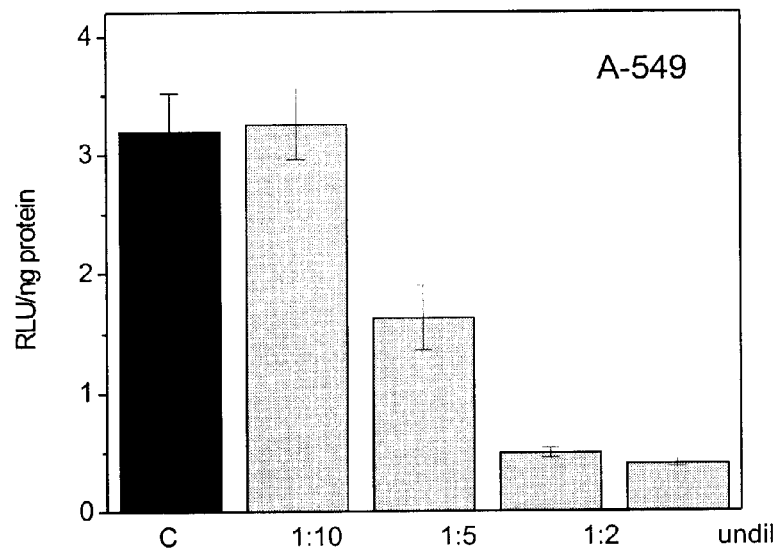
FIGS. 8A, 8B, show the dose-dependent inhibition effect of the second fraction from the FPLC separation, P2, at various concentrations, on LPS-induced iNOS promoter activity in A-549 and mouse marcophage, respectively.
Figure 8B:
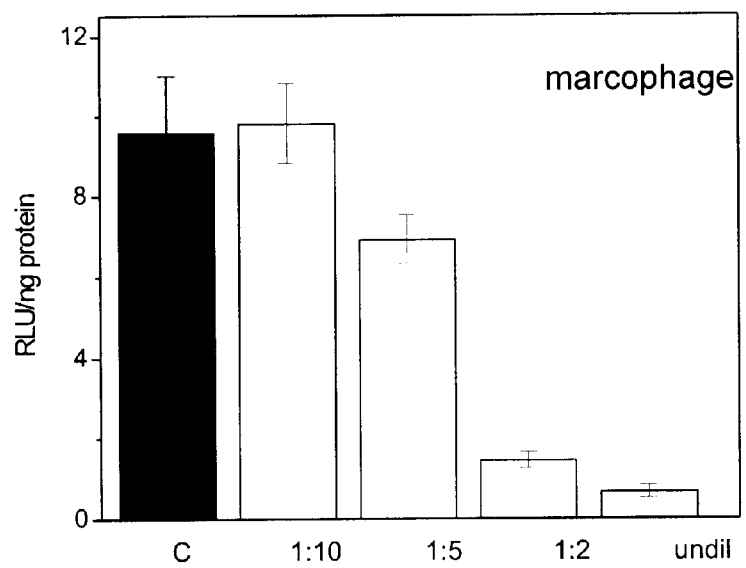

The product in P2 inhibits COX-2 promoter activity and iNOS promoter activity (FIGS. 7 and 8). The promoter activity is performed by transfecting cells such as fibroblasts with a luciferase expression plasmid containing a COX-2 or iNOS promoter fused to luciferase gene. Promoter activity is stimulated with phorbol esters, interleukin-1, tumor necrosis factor-α, lipopolysaccharide, and interferon-gamma. Addition of the product in P2 almost completely inhibits the promoter activity of COX-2 and iNOS. There is a concentration-dependent suppression by P2.

Figure 9:
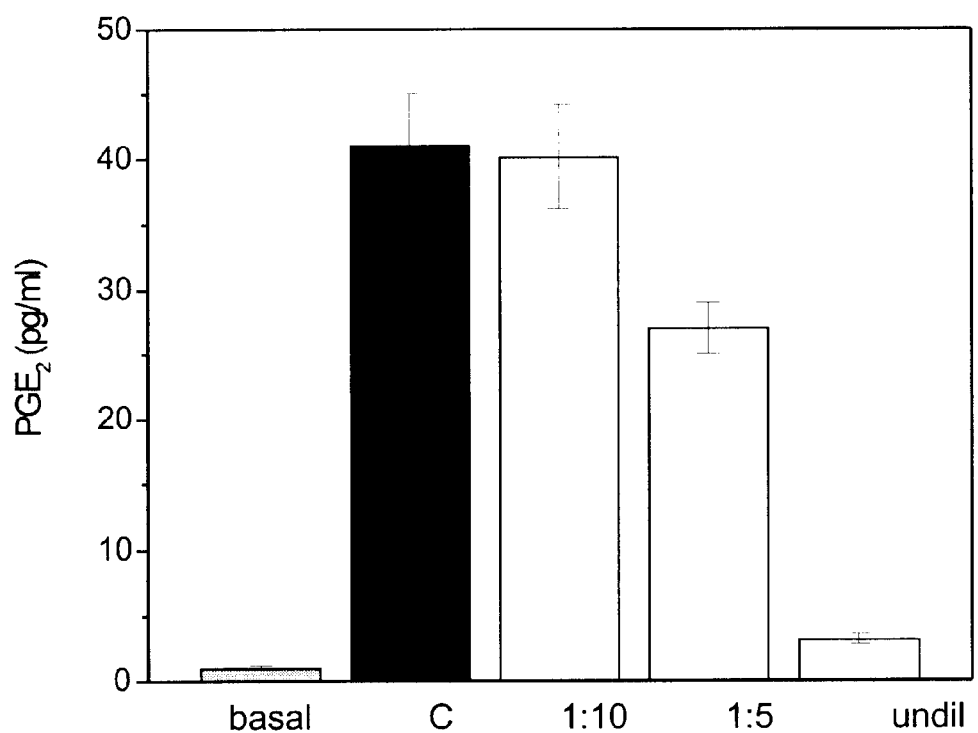
FIG. 9 shows the dose-dependent inhibition effect of the second fraction from the FPLC separation, P2, at various concentrations, on PMA-induced PGE2 level in HFF.

This product inhibits prostaglandin $E_2$ production in inflammatory cells, also in a concentration-dependent manner (FIG. 9).

Tumor cells induce angiogenesis and the newly formed capillaries allow nutrients to be transported into the tumor mass. Angiogenesis plays a crucial role in tumor growth. The product in P2 inhibits tumor-induced angiogenesis (FIG. 10).

Analysis of the product in H4 by mass spectrometry indicates that the product(s) has a molecular weight of 604 daltons. A minor peak has a molecular weight of 779 daltons.

NMR analysis of H4 shows that the product is a derivative of trypophan or trypophan-like molecule. Fluorescence spectroscopy shows that the product contains intrinsic fluorescence and the spectra is superimposed with those of trypophan, confirming that the product contains a tryptophan-like moiety.

In summary, a new product has been invented from cells that has potent inhibitory action on COX-2 and iNOS. This product provides new therapeutic strategy for treating human inflammatory diseases, tissue damage, stroke, septic shock and cancer.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for treating human inflammatory diseases, tissue damage, stroke, septic shock and cancer by administering into a human body an effective amount of a chemical composition, wherein said chemical composition containing a chemical compound or a derivative of said chemical compound, said chemical compound or said derivative of said chemical compound exhibits concurrent COX-2 and iNOS suppressing activities, and said chemical compound is purified from a cultured medium which is produced from a process comprising the following steps:

(a) washing human foreskin fibroblasts with a fresh DMEM medium then incubated in a fresh medium containing 2.5%–10% fetal bovine serum for at least 8 hours to form a proliferating phase medium (PPM);

(b) subjecting said proliferating phase medium to a 10-kDa ultrafiltration membrane to separate said proliferating phase medium into a <10 kDa fraction, which passes through said 10-kDa ultrafiltration membrane, and a >10 kDa fraction, which is retained by said 10-kDa ultrafiltration membrane;

(c) Chromatographing said <10 kDa fraction on a Superdex 30 column by FPLC to separate said <10 kDa fraction into first, second, third, fourth, and fifth post-FPLC fractions, which are observed as five peaks at a spectra absorbance at 220 nm and numbered based on their elusion times from said Superdex 30 column;

(d) Injecting said second post-FPLC fraction into a $C_{18}$ column in a HPLC system with a gradient elute from 10% to 50% acetonitrile and water containing 0.1% trifluoroacetic acid, to separate said second post-FPLC fraction into first, second, third, fourth, and fifth post-HPLC fractions, which are observed as five peaks at a spectra absorbance at 220 nm and numbered based on their elusion times from said $C_{18}$ column; and (e) collecting said fourth post-HPLC fraction.

2. The method according to claim 1 wherein said chemical compound has a molecular weight of about 604 daltons measured by mass spectrometry.

3. The method according to claim 1 said mass spectrometry also contains a minor M/2 peak having a molecular weight of about 779 daltons.

4. The method according to claim 1 wherein said chemical compound is a derivative of trypophan or trypophan-like molecule as shown by fluorescence spectroscopy.

* * * * *